(12) United States Patent
Lai et al.

(10) Patent No.: US 11,123,434 B2
(45) Date of Patent: Sep. 21, 2021

(54) DRUG DELIVERY DEVICE AND ITS METHOD OF MANUFACTURE

(71) Applicant: City University of Hong Kong, Kowloon (HK)

(72) Inventors: Wing Fu Lai, Aberdeen (HK); Andrei Rogatch, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/656,228

(22) Filed: Jul. 21, 2017

(65) Prior Publication Data

US 2019/0022233 A1    Jan. 24, 2019

(51) Int. Cl.
| | |
|---|---|
| *A61K 47/36* | (2006.01) |
| *A61K 9/06* | (2006.01) |
| *A61K 9/16* | (2006.01) |
| *A61K 31/7088* | (2006.01) |
| *A61K 38/00* | (2006.01) |
| *C08F 251/00* | (2006.01) |
| *C08J 9/00* | (2006.01) |
| *C08J 9/28* | (2006.01) |
| *C08F 299/00* | (2006.01) |
| *C08F 290/10* | (2006.01) |
| *B01J 13/00* | (2006.01) |
| *C08J 9/32* | (2006.01) |

(52) U.S. Cl.
CPC ............... *A61K 47/36* (2013.01); *A61K 9/06* (2013.01); *A61K 9/1635* (2013.01); *A61K 31/7088* (2013.01); *A61K 38/00* (2013.01); *B01J 13/0065* (2013.01); *C08F 251/00* (2013.01); *C08F 290/10* (2013.01); *C08F 299/00* (2013.01); *C08J 9/0061* (2013.01); *C08J 9/283* (2013.01); *C08J 9/32* (2013.01); *C08J 2201/026* (2013.01); *C08J 2201/0524* (2013.01); *C08J 2205/022* (2013.01); *C08J 2207/10* (2013.01); *C08J 2303/04* (2013.01); *C08J 2335/02* (2013.01); *C08J 2351/02* (2013.01)

(58) Field of Classification Search
CPC ..... A61K 47/36; C08F 299/00; C08F 290/10; B01J 13/0065
See application file for complete search history.

(56) References Cited

U.S. PATENT DOCUMENTS

| | | | | |
|---|---|---|---|---|
| 8,242,179 | B2 * | 8/2012 | Chudzik | A61F 2/441 514/772.3 |
| 8,513,322 | B2 * | 8/2013 | Wright | C08F 2/34 522/153 |
| 8,617,132 | B2 | 12/2013 | Golzarian et al. | |

FOREIGN PATENT DOCUMENTS

| | | |
|---|---|---|
| CA | 2777083 A1 | 4/2011 |
| CN | 1872078 A | 12/2006 |
| EP | 2485777 B1 | 12/2013 |
| EP | 2626088 B1 | 12/2014 |
| KR | 100233550 B1 | 12/1999 |
| WO | 2011044236 A1 | 4/2011 |

OTHER PUBLICATIONS

Ferreira Prep. gels sucrose glycidyl methacrylate, Carbohydrate polym. p. 15 (Year: 2000).*
Leach Photocrosslinkable hyaluronic acid-PEG Glycol hydrogel Biomaterials p. 125 (Year: 2005).*
Heidin Starch modified with glycidyl methacrylate Carbohydrate Polymers p. 606 (Year: 2010).*

* cited by examiner

*Primary Examiner* — Matthew P Coughlin
*Assistant Examiner* — Thurman Wheeler
(74) *Attorney, Agent, or Firm* — Renner, Kenner, Greive, Bobak, Taylor & Weber

(57) ABSTRACT

The invention relates to a drug delivery device adapted for carrying and delivering both hydrophilic and lipophilic drug molecules. The drug delivery device includes a porous body for adsorption of drug molecules, the body including a plurality of microspheres, and a hydrogel forming crosslinks connecting the plurality of microspheres.

9 Claims, 21 Drawing Sheets

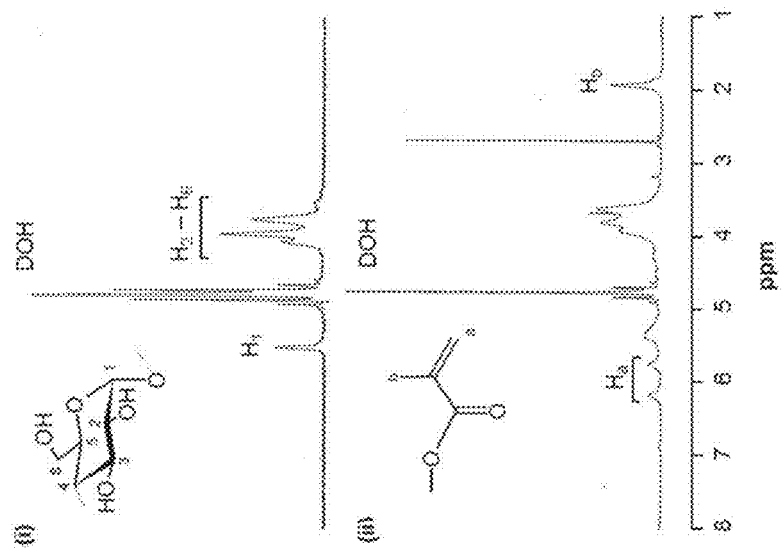
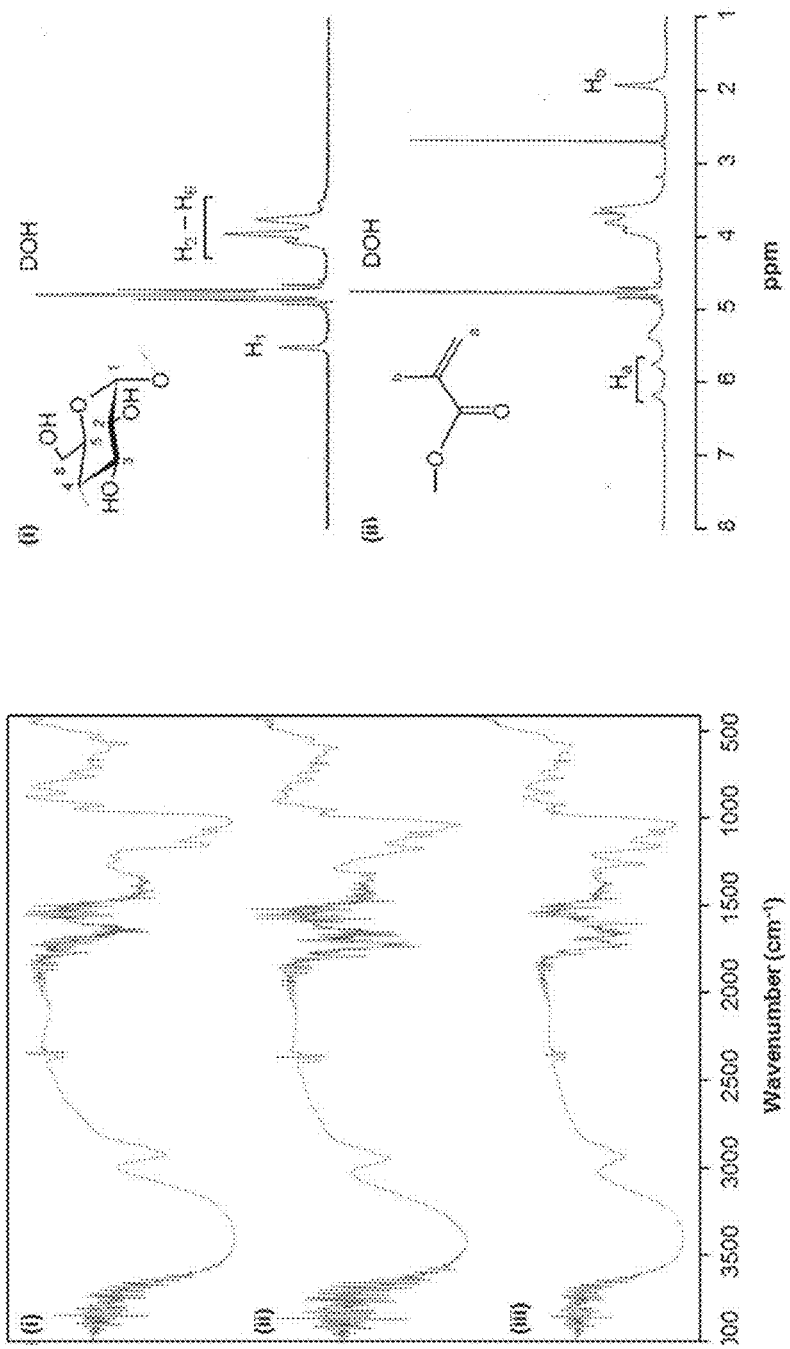
Figure 1C
Figure 1B

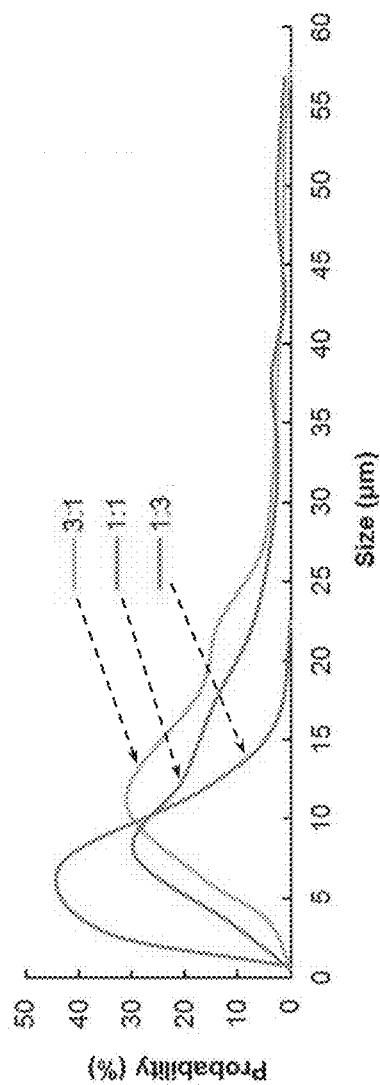
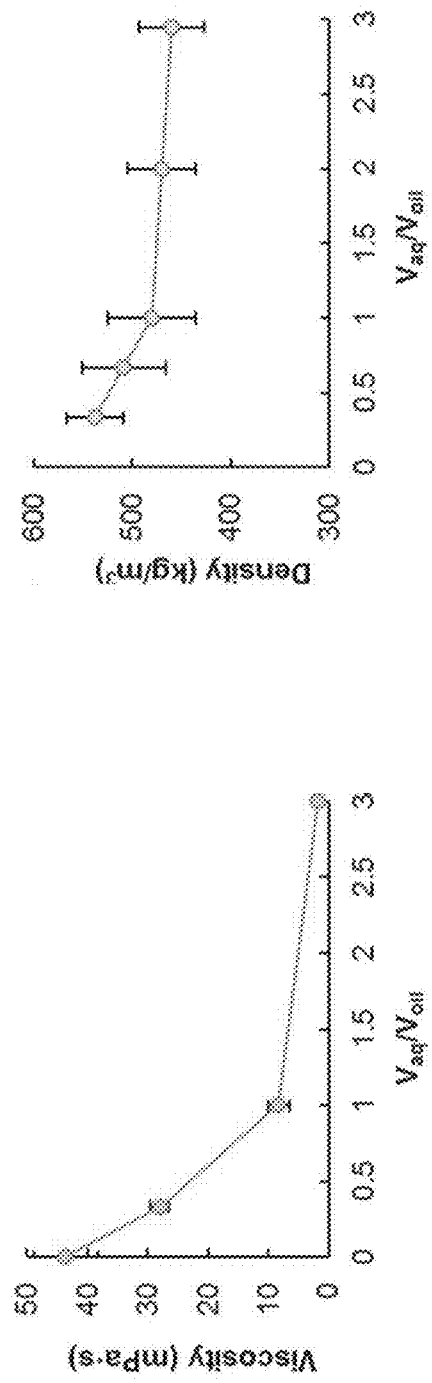
Figure 5B
Figure 5C
Figure 5D

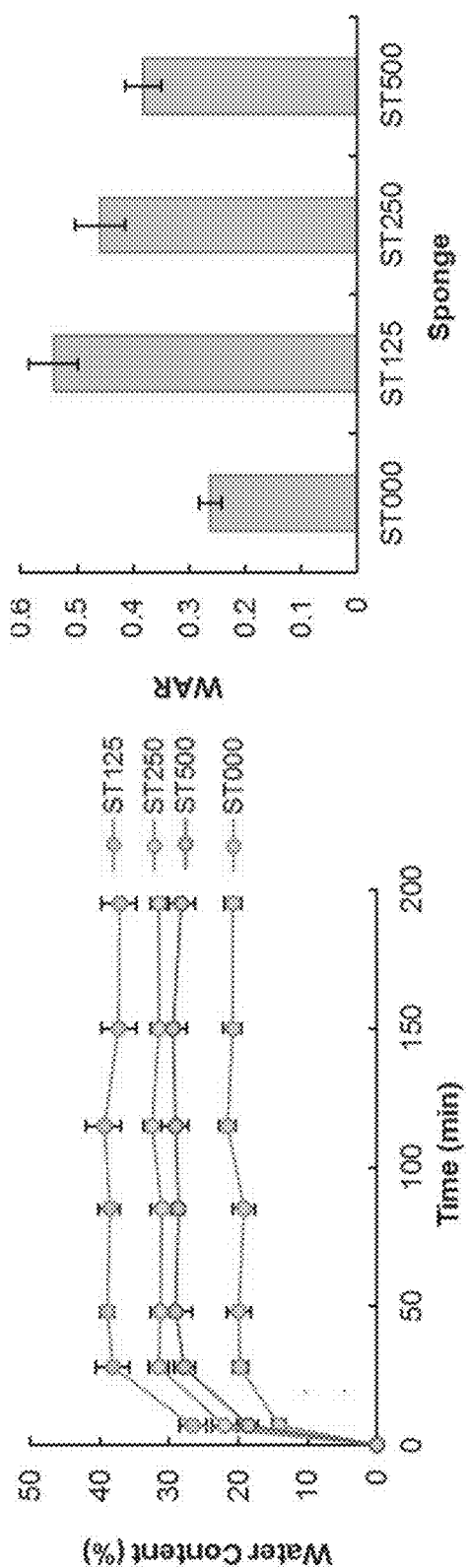
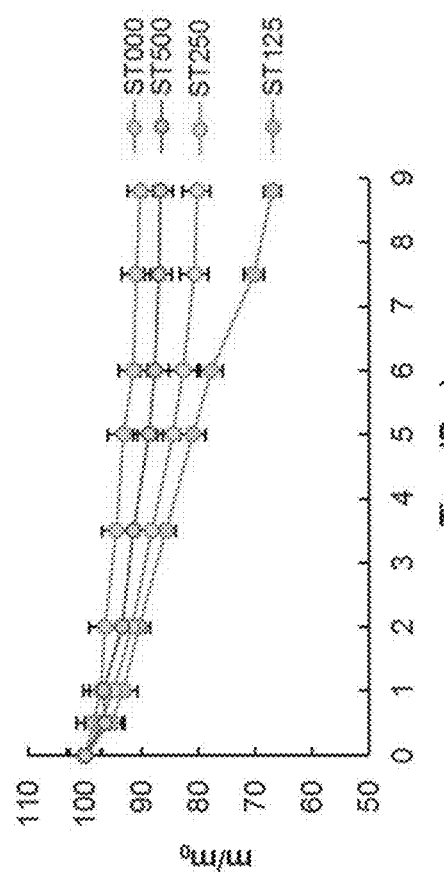
Figure 8A
Figure 8B
Figure 8C

DRUG DELIVERY DEVICE AND ITS METHOD OF MANUFACTURE

TECHNICAL FIELD

The present invention relates to a drug delivery device, and particularly, although not exclusively, a drug delivery device that can effectively deliver both lipophilic and hydrophilic drugs, for example for multi-drug therapy.

BACKGROUND

Various drug carriers have been developed for therapeutic applications such as in vivo drug delivery. In general, a drug carrier is loaded with drugs, through mechanical or chemical means, and is then injected or implanted into the subject for controlled release of the drugs. Depending on applications, the drug carrier may be loaded with different drugs. In single-drug therapy, the carrier is loaded with one type of drugs; and in multi-drug therapy, the carrier is loaded two or more types of drugs (with different chemical properties). Compared with single-drug therapy, multi-drug therapy has attracted extensive interests because of its potential to offer higher therapeutic efficacy.

One of the predominant factors affecting the loading of the drugs in drug carriers is the affinity of the drug molecules to the system. The efficiency of the loading process in existing single- and multi-drug delivery systems is largely affected by the hydrophilicity and lipophilicity of the drug molecules. In practice, the amount of the loaded drug, whose hydrophilic or lipophilic nature is opposite to that of the system, may be too low to give any significant therapeutic effect, thereby limiting therapeutic efficiency.

Thus there is a need for a drug carrier that is easy to produce and can effectively and flexibly be adapted to load and deliver different types of drugs.

SUMMARY OF THE INVENTION

In accordance with a first aspect of the present invention, there is provided a drug delivery device adapted for carrying and delivering both hydrophilic and lipophilic drug molecules, comprising: a porous body for adsorption of drug molecules, comprising: a plurality of microspheres, and a hydrogel forming cross-links connecting the plurality of microspheres.

In one embodiment of the first aspect, the porous body possesses a sponge-like architecture.

Preferably, the microspheres each contain one or more acrylate groups.

Preferably, the microspheres are formed by trimethylolpropane ethoxylate triacrylate, trimethylolpropane triacrylate, or their derivative.

Preferably, the microspheres are poly(trimethylolpropane ethoxylate triacrylate) microspheres.

In one embodiment of the first aspect, the hydrogel is formed by a starch-based derivative that is preferably modified with a methacrylate source.

In one embodiment of the first aspect, the starch-based derivative is in the form of:

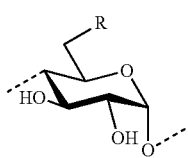

where R is

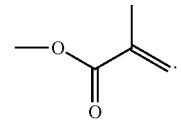

In one embodiment of the first aspect, the drug delivery device is adapted for simultaneous delivery of at least one type of hydrophilic drug molecules and at least one type of lipophilic drug molecules.

In one embodiment of the first aspect, the drug delivery device is adapted for simultaneous delivery of at least two different types of drugs molecules with different aqueous solubility.

In one embodiment of the first aspect, the drug delivery device further includes at least one type of hydrophilic drug molecules adsorbed on the body.

In one embodiment of the first aspect, the drug delivery device further includes at least one type of lipophilic drug molecules adsorbed on the body.

In one embodiment of the first aspect, the drug delivery device further includes at least one type of lipophilic drug molecules and at least one type of hydrophilic drug molecules adsorbed on the body.

In accordance with a second aspect of the present invention, there is provided a drug delivery device adapted for carrying and delivering both hydrophilic and lipophilic drug molecules, comprising: a porous body for adsorption of drug molecules, comprising: a plurality of poly(trimethylolpropane ethoxylate triacrylate) microspheres, and a hydrogel formed by a starch-based derivative, the hydrogel forming cross-links connecting the plurality of microspheres.

In one embodiment of the second aspect, the starch-based derivative is in the form of:

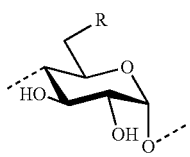

where R is

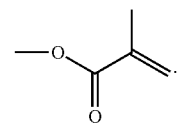

In accordance with a third aspect of the present invention, there is provided method of producing a drug delivery device, comprising: dispersing precursors for microsphere formation in an aqueous solution containing a hydrogel formation; mixing the resulting mixture to form an emulsion; and curing the emulsion using ultraviolet light or corresponding energy source to form a porous body adapted for adsorption of drug molecules, the porous body being formed by: a plurality of microspheres, and a hydrogel forming cross-links connecting the plurality of microspheres.

In one embodiment of the third aspect, the method further includes preparing precursors for hydrogel formation.

Preferably, the step of preparing the precursors for hydrogel formation comprises: subjecting starch to a methacrylate source, using catalyst, to form target molecules; subjecting the mixture containing the target molecules to initiator molecules; and curing the resulting mixture with ultraviolet light or corresponding energy source so as to cross-link the target molecules.

Preferably, the step of subjecting starch to the methacrylate source is performed at 50° C.

Preferably, the catalyst comprises 4-Dimethylaminopyridine.

Preferably, the target molecules are in the form of

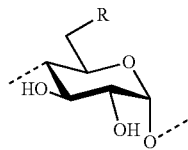

where R is

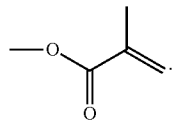

Preferably, the microspheres are formed by trimethylolpropane ethoxylate triacrylate, trimethylolpropane triacrylate, or their derivative.

Preferably, the microspheres are poly(trimethylolpropane ethoxylate triacrylate) microspheres.

Preferably, the method further includes adsorbing drug particles on the porous body.

BRIEF DESCRIPTION OF THE DRAWINGS

Embodiments of the present invention will now be described, by way of examples, with reference to the accompanying drawings in which:

FIG. 1B is the Fourier transform infrared spectroscopy (FTIR) spectra of (i) starch, (ii) target molecule "starMA", and (iii) cross-linked "starMA";

FIG. 1C is nuclear magnetic resonance (NMR) spectra of (i) starch and (ii) "starMA";

FIG. 5B is a graph showing size distribution of the microspheres in sponges with different $V_{aq}/V_{oil}$ values (the overall concentration of "starMA" therein is 2.5 w/v %);

FIG. 5C is a graph showing changes in the viscosity of the emulsion, with different $V_{aq}/V_{oil}$ values, before UV cure;

FIG. 5D is a graph showing changes in the density of the sponge against changes in the $V_{aq}/V_{oil}$ values (the overall concentration of "starMA" therein is 2.5 w/v %);

FIG. 8A is a graph showing the changes in the water content of the sponge as a function of time at pH 7.4;

FIG. 8B is a graph showing the WAR of different sponges after immersion in PBS (at pH 7.4) for 3 hours;

FIG. 8C is a graph showing the effect of erosion on different sponges at the pH of 7.4;

DETAILED DESCRIPTION OF THE PREFERRED EMBODIMENT

Figure 4A:
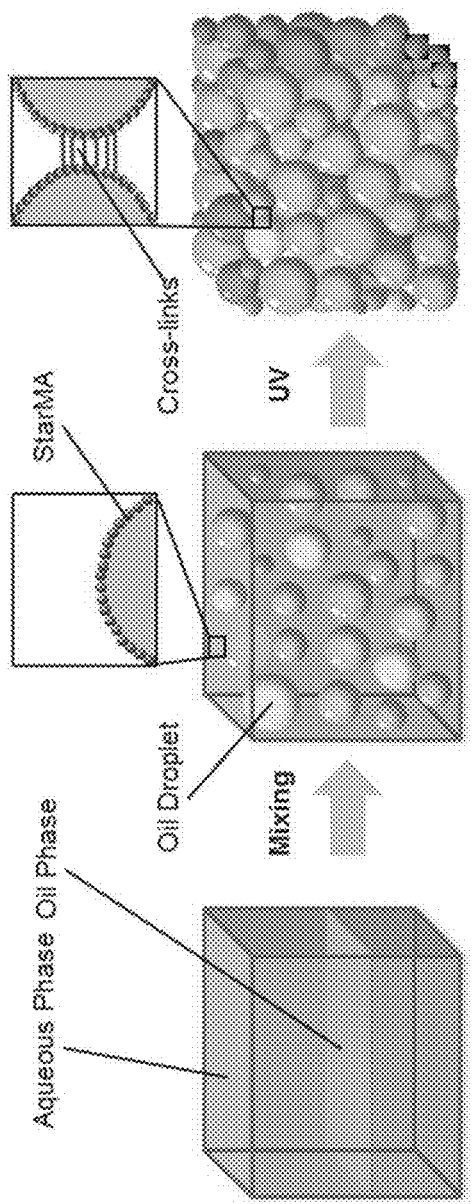
FIG. 4A is a schematic diagram illustrating a one-pot process for generation of the microsphere hydrogel sponge in accordance with one embodiment of the present invention.

Referring to FIG. 4A, there is shown a drug delivery device adapted for carrying and delivering both hydrophilic and lipophilic drug molecules, comprising: a porous body for adsorption of drug molecules, comprising: a plurality of microspheres, and a hydrogel forming cross-links connecting the plurality of microspheres. Preferably, the porous body possesses a sponge-like architecture. In a preferred embodiment, the microspheres each contains one or more acrylate groups, and they may be formed by trimethylolpropane ethoxylate triacrylate (TMPETA), trimethylolpropane triacrylate, or their derivative. Preferably, the microspheres are poly(trimethylolpropane ethoxylate triacrylate) microspheres. The hydrogel is preferably formed by a starch-based derivative modified with a methacrylate source, such as "starMA" as described in further detail below.

In the present invention, the drug delivery device is adapted for simultaneous delivery of at least one type of hydrophilic drug molecules and at least one type of lipophilic drug molecules, or essentially, at least two different types of drugs molecules with different aqueous solubility.

Synthesis and Structural Characterization of Target Molecule "StarMA"

Figure 1A:
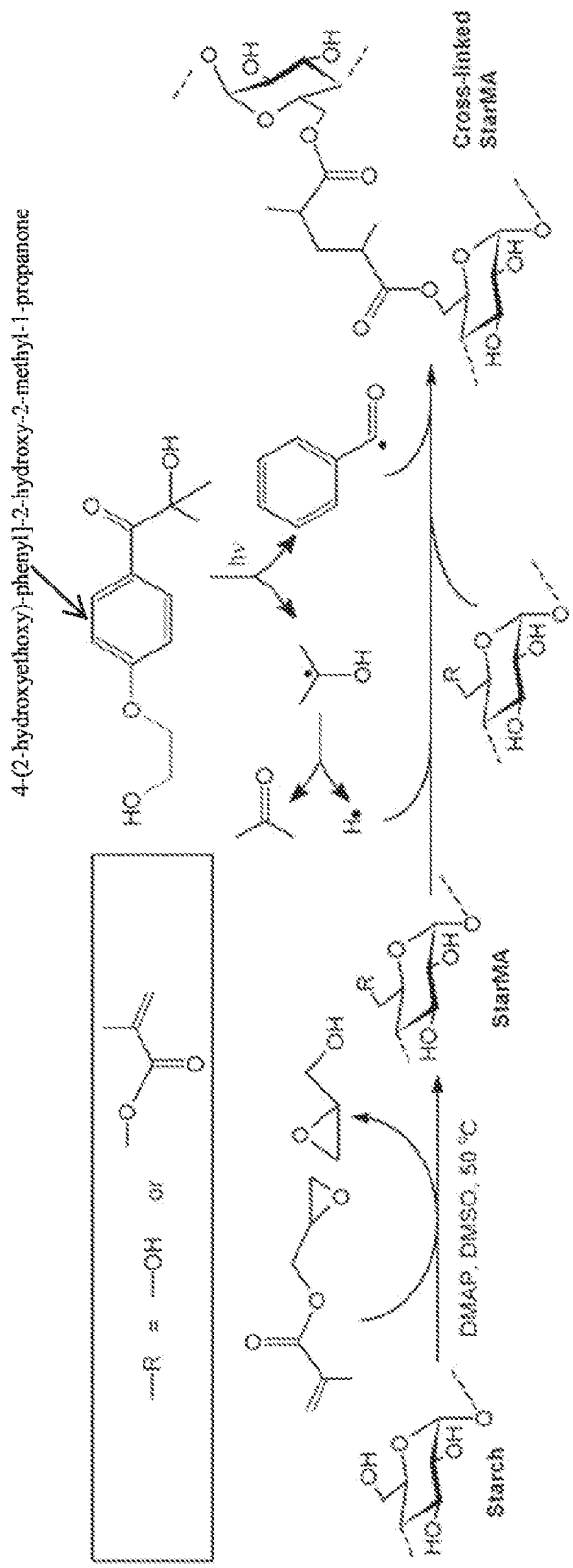
FIG. 1A is a synthetic scheme of a wettable polymeric matrix in accordance with one embodiment of the present invention.

As shown in FIG. 1A, in one embodiment of the present invention, target molecule "StarMA" (MA stands for methacrylate) is synthesized by modification of starch using a methacrylate source and catalyst. The methacrylate source may be glycidyl methacrylate. DMAP may be used as a catalyst. The reaction is preferably performed at 50° C. Two reaction routes may be involved during this starch modification process: transesterification and epoxide ring-opening mechanisms. However, as a polar aprotic solvent DMSO is used as a reaction medium in this study, trans-esterification will be the predominant reaction route.

FIG. 1B illustrates the structure of starMA so generated using FTIR. Referring to FIG. 1B, the peaks at 1,730 cm$^{-1}$ and 1657 cm$^{-1}$ in the spectrum of starMA (spectrum (ii)) are assigned to the carbonyl signal from the introduced methacrylate group (C=O stretch peak) and to the C=C stretch of the unsaturated carbon atoms, respectively. Compared to native starch (spectrum (i)), starMA has stronger signals in the wavenumber range between 2850 cm$^{-1}$ and 3000 cm$^{-1}$. These signals are due to C—H stretch vibration. The amplification of the signal in starMA is caused by the supplementary $CH_3$ groups from the introduced methacrylate groups.

Successful generation of starMA is further verified using $^1$H-NMR, as shown in FIG. 1C. In the spectrum of starch (spectrum (i)) as shown, a representative signal from starch can be found at 5.3 ppm, and this is attributed to the proton at the anomeric carbon of the α-1, 4 linkages. This signal is distinctively separated from the various peaks that span between 3.5 and 4.2 ppm (from starch). All these signals can be found in the spectrum of starMA (spectrum (ii)), which possesses a signal from the methyl protons of the methacryloyl group (1.9 ppm). In spectrum (ii) characteristic peaks can also be found at around 5.9 and 6.2 ppm. These peaks are assigned to the protons from the double bond in the methacryloyl group. Based on the proton integral values of peaks at 5.3 ppm and 1.9 ppm in the spectrum of starMA, the degree of substitution is approximated to be 33%.

Figure 2A:
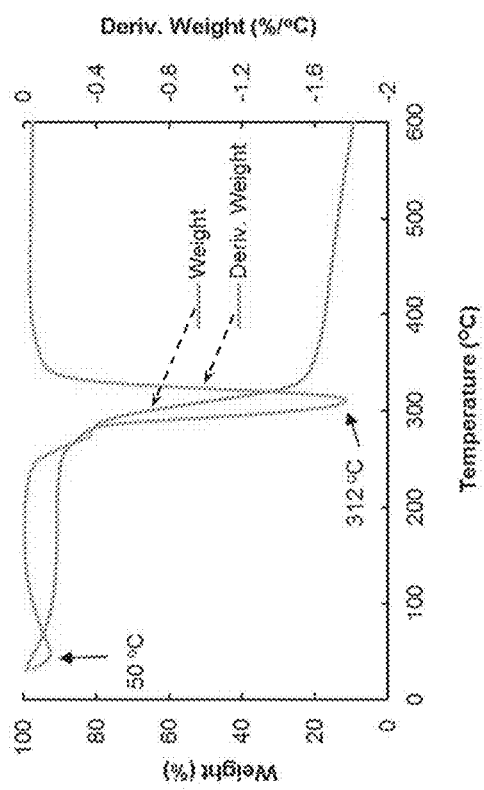
FIG. 2A is a graph showing thermogravimetric (TGA) and differential thermogravimetric (DTGA) curves for starch.
Figure 2B:
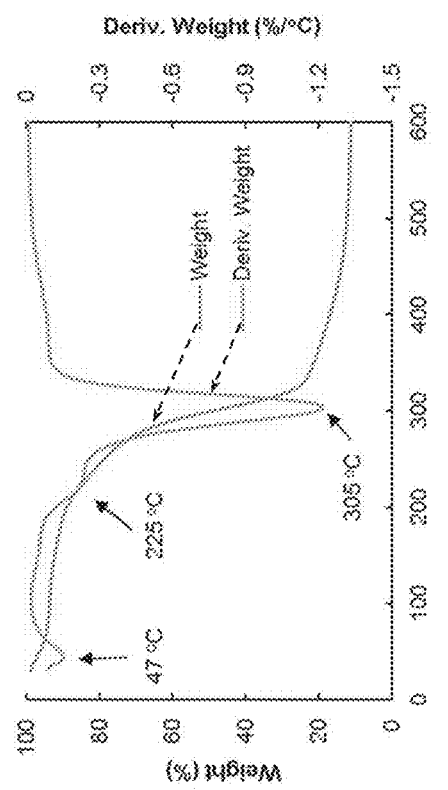
FIG. 2B is a graph showing thermogravimetric (TGA) and differential thermogravimetric (DTGA) curves for "starMA"

The occurrence of starch modification was further confirmed by TGA and DTGA, as illustrated in FIGS. 2A and 2B. As shown in FIG. 2A, the TGA profile of starch shows two distinct zones of weight loss. The first one is at around 30-120° C. This weight loss is attributed to the evaporation of the traces of moisture present. The second zone is around 250-350° C., which is contributed by the degradation of the starch backbone. Also in FIG. 2A, the differential TGA curve of starch also reveals that the temperatures for the quickest weight loss in two stages are at around 50 and 312° C. As seen from FIG. 2B (the corresponding graph for StarMA), while these two weight loss zones also appear in the TGA profile after modification of starch with glycidyl methacrylate, at least one extra zone of weight loss is identified at 225° C. Such a change in thermal behaviour as compared to that of native starch is attributed to the presence of methacrylate groups.

Due to the presence of the methacrylate group, in the present embodiment starMA can be cross-linked. In one example, 1-[4-(2-hydroxyethoxy)-phenyl]-2-hydroxy-2-methyl-1-propanone is used as the initiator for the cross-linking process. During the cross-linking process, the initiator molecule is cleaved by UV (or equivalent energy source) to produce free-radicals, which can be attracted with a molecule of starMA. This opens the double-bond in the starMA molecule, generating a new radical center for the cross-linking process.

A similar mechanism of cross-linking is preferably applied to subsequent generation of microspheres from TMPETA during fabrication of the microsphere hydrogel sponge (described below). As TMPETA possesses three acrylate groups in each molecule, the acrylate group can undergo radical-induced cross-linking reactions similar to those undergone by the methacrylate group of starMA.

"StarMA" as a Bifunctional Emulsion Stabilizer

Figure 3A:
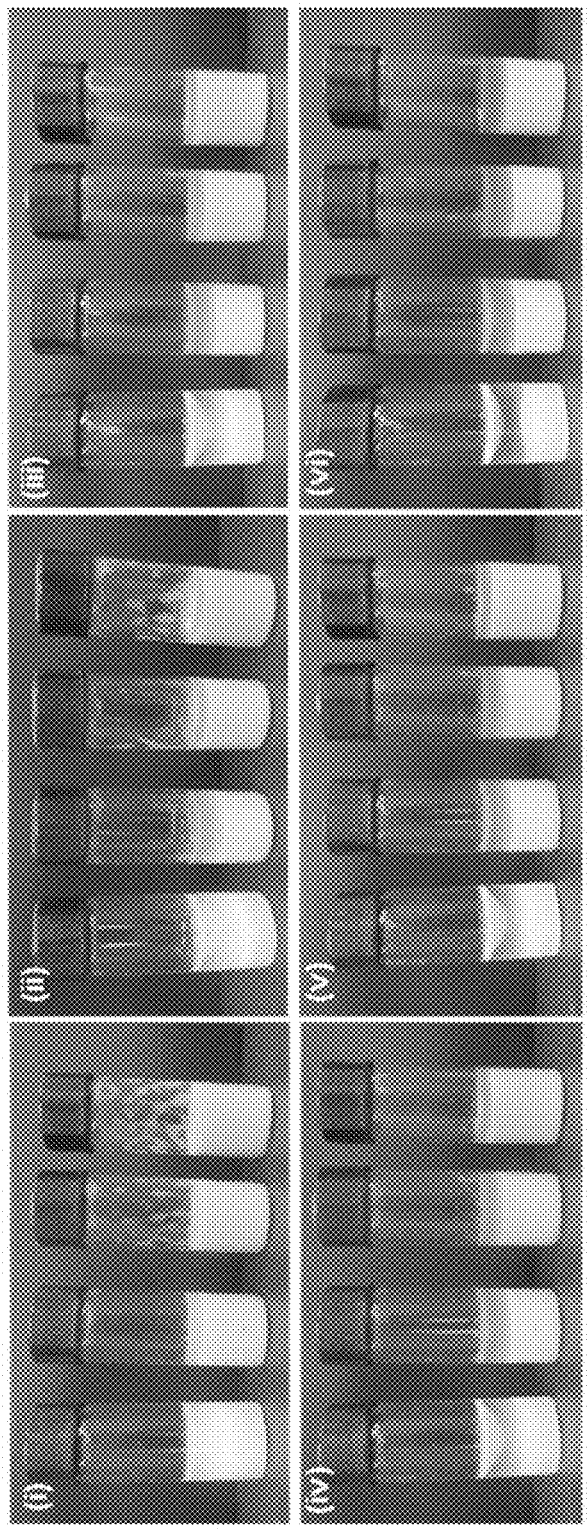
FIG. 3A shows pictures illustrating phase separation of emulsions with different concentrations of "starMA" (i) on production, and after storage for (ii) 10 min, (iii) 30 min, (iv) 45 min, (v) 1 hour, and (vi) 2 hours, wherein the emulsion samples, from left to right, are ST000, ST125, ST250 and ST500, respectively.

The stability of the water-and-oil emulsion, in which starMA of the present embodiment is added into the aqueous phase at different concentrations, is evaluated based on the rate of phase separation, as shown in the pictures of FIG. 3A. As seen from FIG. 3A: Initially, all emulsions are milky. After to minutes, the emulsions exhibit different levels of phase separation, with the degree of sedimentation being inversely related to the concentration of starMA present. In particular, the water-and-oil emulsion containing 5 w/v % of starMA exhibits the highest stability among all emulsions examined, as they display negligible phase separation for at least the first 45 minutes after preparation of the emulsion.

To determine the identity of the two phases in the emulsion, Oil Red O (ORO) stain is added into the emulsion to stain the oil phase. Results show that oil and water function as the dispersed and continuous phases, respectively. This is due to the higher solubility of starMA in the aqueous phase than in the oil phase, and is consistent with the Bancroft's rule which states that the liquid in which the emulsifier has a higher solubility forms the continuous phase.

Figure 3D:
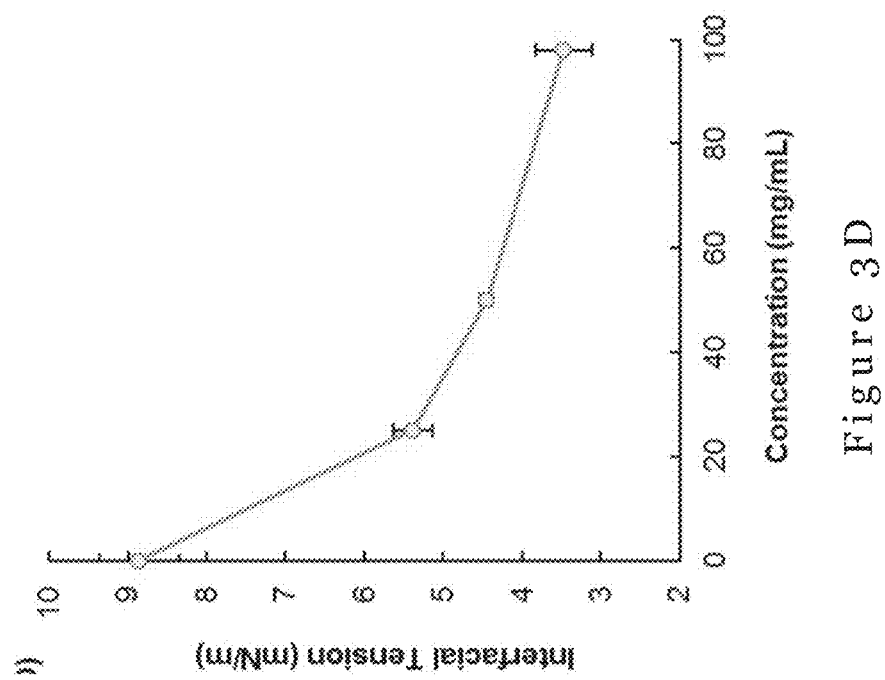
FIG. 3D shows a graph illustrating changes in the interfacial tension between the oil phase (TMPETA, with 10% 1-[4-(2-hydroxyethoxy)-phenyl]-2-hydroxy-2-methyl-1-propanone) and the aqueous phase against the concentration of "starMA" in the aqueous phase.
Figure 3B:
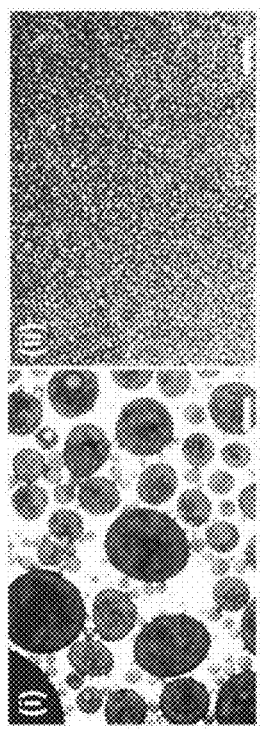
FIG. 3B shows optical images of the (i) water/TMPETA emulsion and (ii) target molecule "starMA"/TMPETA emulsion, where the overall concentration of "starMA" is 2.5 w/v % (the scale bar represents 200 m)
Figure 3C:
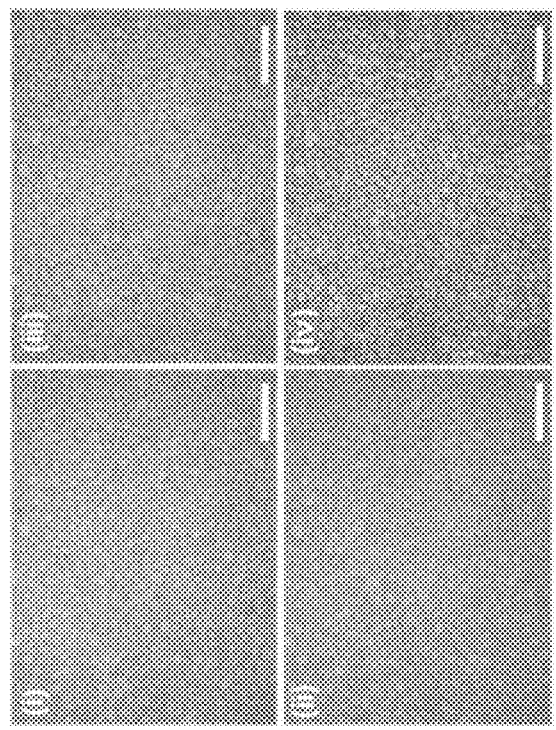
FIG. 3C shows optical images of droplets of the "starMA"/TMPETA emulsion (i) on production, and after storage for (ii) 2 min, (iii) 10 min, and (iv) 30 min, where the overall concentration of "starMA" is 2.5 w/v % (the scale bar represents 200 m)

To confirm the effect of starMA as an emulsion stabilizer, the morphological changes of emulsion droplets are evaluated using bright field microscopic analysis, results shown in FIG. 3B. As seen, the emulsion produced in the absence of starMA has significantly larger droplets as compared to that containing 2.5 w/v % starMA. Also, in the presence of starMA, changes in the size of the droplets are negligible even after storage for 30 min, as shown in FIG. 3C. The emulsion stabilizing effect of starMA is partially attributed to its capacity to reduce the interfacial tension between the oil phase and the aqueous phase, as shown in FIG. 3D. As the process of emulsion depends largely on a stress balance between the interfacial tension that tends to hold droplets together and the forces that leads to the droplet breakup, the ability to reduce the interfacial tension can improve the stability of an emulsion.

Generation of the Microsphere Hydrogel Sponge

Figure 4B:
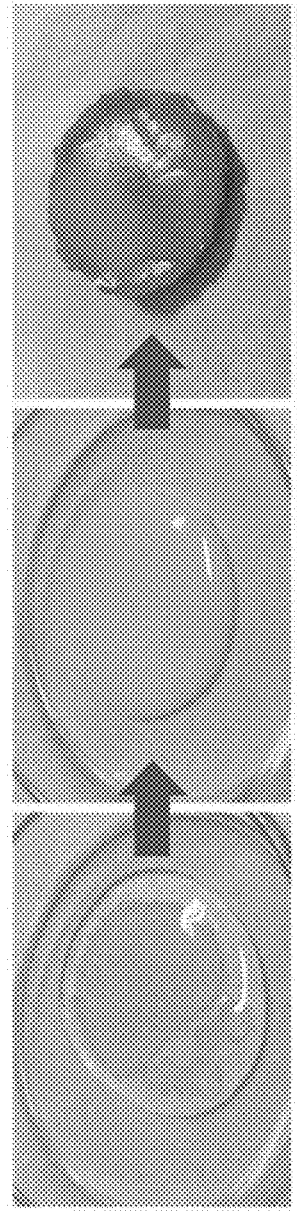
FIG. 4B shows pictures showing different stages of the sponge fabrication process.
Figure 4C:
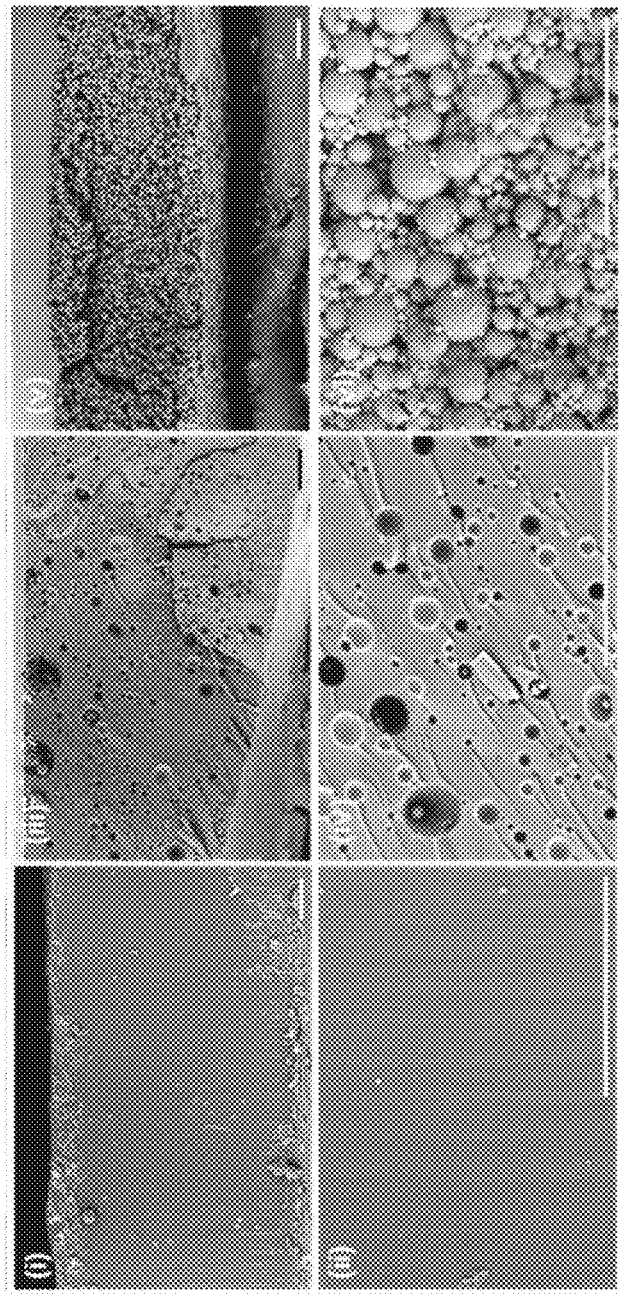
FIG. 4C shows the SEM images of (i-ii) UV-cured TMPETA and (iii-vi) the microsphere hydrogel sponges, where the overall concentrations of "starMA" in the microsphere hydrogel sponges are (iii-iv) 0 w/v % and (v-vi) 2.5 w/v % (the low and high magnification images are shown in the upper and lower columns, respectively; and the scale bar represents 200 μm).

In one embodiment of the present invention, as shown in FIGS. 4A and 4B, a one-pot process is applied for generation of the microsphere hydrogel sponge. In the present invention, starMA functions both as a cross-linker and an emulsion stabilizer. The SEM images of UV-cured TMPETA (without starMA) and the microsphere hydrogel sponges are shown in FIG. 4C. The results show that cured TMPETA (without starMA) has a highly compact, barely porous structure. This can be explained by the following: When TMPETA is mixed with water before generation of a sponge upon UV cure, TMPETA is dispersed as oil droplets, suspending in the continuous aqueous phase. However, due to the instability of the emulsion, coalescence of the oil droplets occurs almost immediately after emulsion formation and throughout the whole process of UV cure. The sponge formed, therefore, only has a very limited amount of discrete pores distributing all over the compact structure of the cured TMPETA. These pores are expected to be formed by some of the aqueous phase being trapped inside the TMPETA phase during UV cure which freezes the process of coalescence.

On the contrary, in the presence of starMA in the present embodiment, the emulsion formed can sustain its stability throughout the UV cure process, and can generate a bulk material consisting of TMPETA microspheres, as illustrated in FIGS. 4A and 4C. During the process of sponge generation, starMA possesses the same functional groups as those in TMPETA molecules, thereby participating in the same UV-initiation polymerization process as TMPETA does. However, due to the immiscibility of the two phases, polymerization reactions between TMPETA and starMA are limited only to the interface between the aqueous and oil phases. The TMPETA microspheres can then be hold together by the starMA hydrogel to form a highly porous structure, which may be used for drug adsorption.

Effects of Volumetric Ratios

Figure 5A:
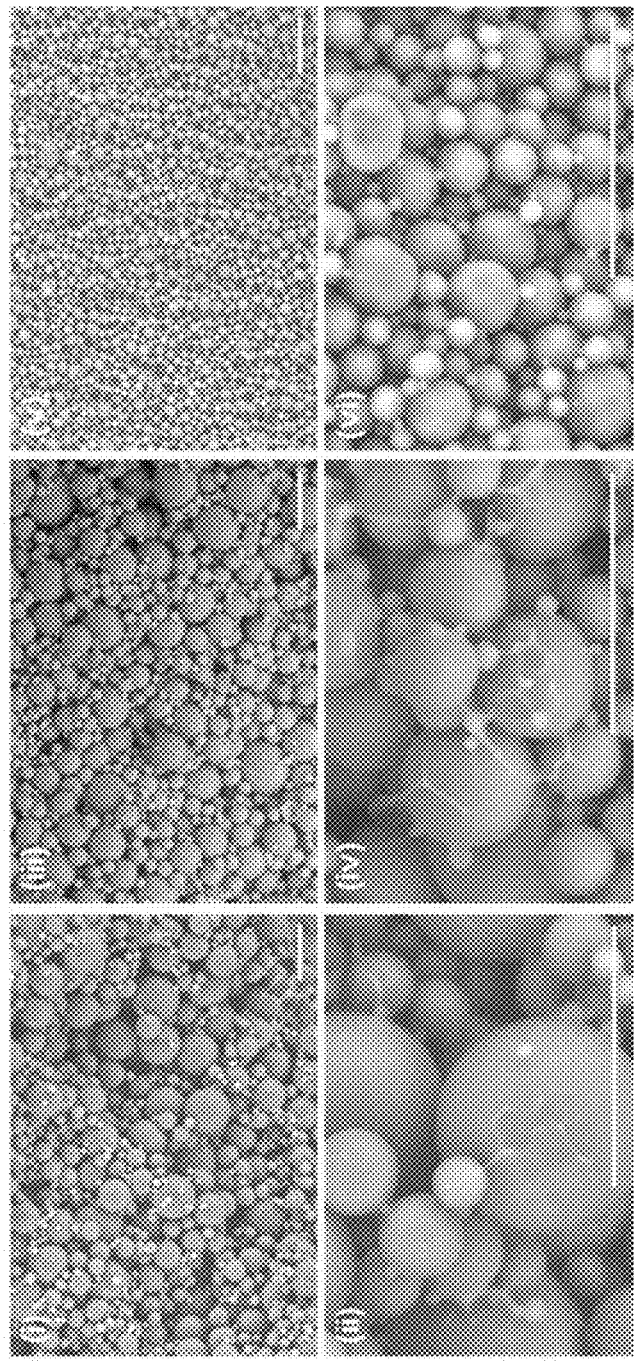
FIG. 5A shows SEM images of sponges with different $V_{aq}/V_{oil}$ values: (i, ii) 3:1, (iii, iv) 1:1, and (v, vi) 1:3 (the scale bar represents 50 m; the overall concentration of "starMA" is 2.5 w/v %)

To optimize the composition of a microsphere hydrogel sponge for drug delivery in the present embodiment, sponges with different $V_{aq}/V_{oil}$ values are generated. The results, shown in FIGS. 5A and 5B, indicate that the diameter of the microspheres in the sponge is positively related to the $V_{aq}/V_{oil}$ value. The decrease in the size of the emulsion droplet has also led to an increase in the viscosity of the system before cure, as shown in FIG. 5C. Also, the decrease in the size of the microspheres may allow the microspheres to pack more closely together, thereby increasing the density of the sponge, as shown in FIG. 5D.

Figure 6A:
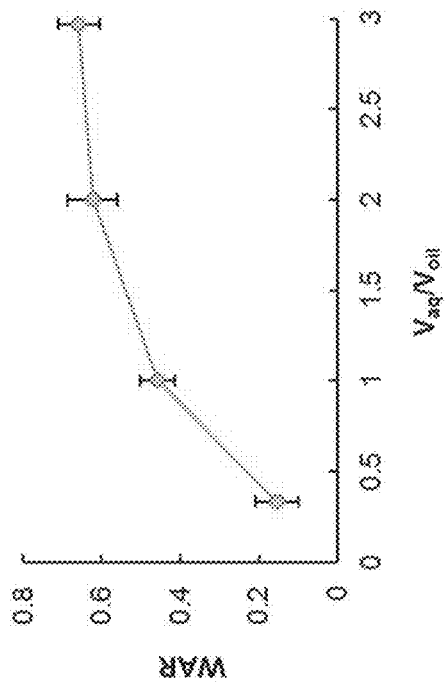
FIG. 6A is a graph showing changes in water content of the sponges, with different $V_{aq}/V_{oil}$ values, as a function of time at pH 7.4 (the overall concentration of "starMA" therein is 2.5 w/v %)
Figure 6B:
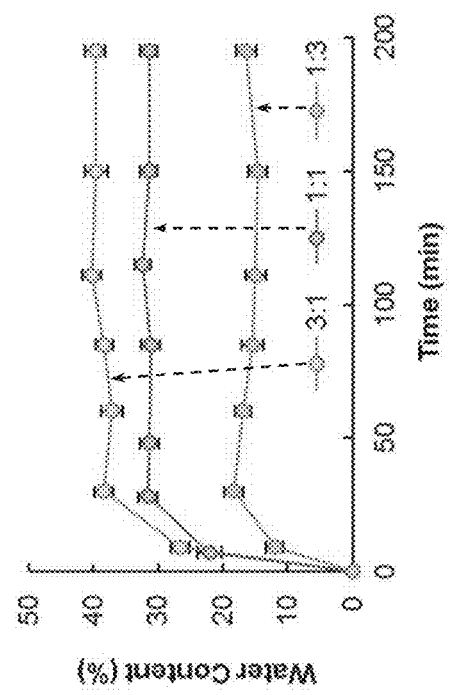
FIG. 6B is a graph showing changes in WAR against changes in the $V_{aq}/V_{oil}$ value of the sponge in PBS (pH 7.4) for 3 hours (the overall concentration of "starMA" therein is 2.5 w/v %)
Figure 6C:
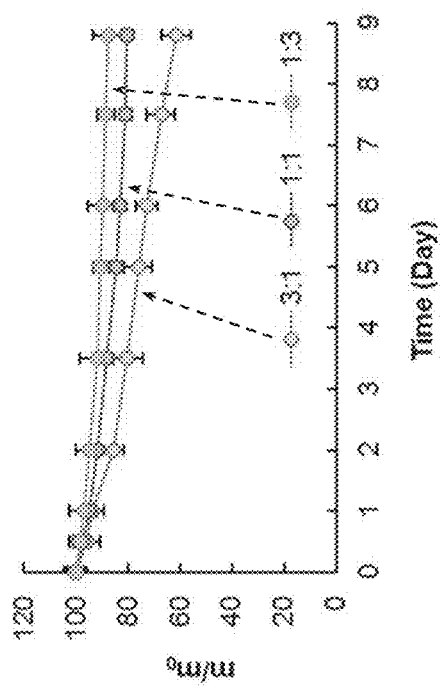
FIG. 6C is a graph showing effect of erosion of the sponges, with different $V_{aq}/V_{oil}$ values, at the pH of 7.4. (the overall concentration of "starMA" therein is 2.5 w/v %)

In the present invention, the capacity of water sorption by the sponge is the result of the combination of several forces including osmotic, capillary and hydration forces. These forces are counterbalanced by the force exerted by the cross-linked microspheres to resist expansion of the network. The magnitudes of these opposing forces determine the equilibrium swollen state of the sponge, and finally influence the mechanical strength and diffusion characteristics. Based on the results in FIGS. 6A-6C, we observe that the $V_{aq}/V_{oil}$ value relates positively with the swelling capacity and WAR of the sponge but negatively with the erosion capacity. This is possibly because microspheres in sponges with a lower $V_{aq}/V_{oil}$ value have smaller size and hence can be more closely packed. The higher density of the sponge, therefore, resists the diffusion of water into the system and hence slows down the rate of erosion. As water in the sponge is the medium through which drug molecules diffuse, the swelling capacity and erosion rate are two important parameters affecting the release rate of the loaded drug. By balancing the swelling capacity and the erosion rate, the $V_{aq}/V_{oil}$ ratio of 1:1 is selected for generation of the sponge for the following studies. It should be noted that the $V_{aq}/V_{oil}$ ratio need not be 1:1 in practice, and can be varied to tailor for different drug applications.

Effects of "StarMA" Concentrations

Figure 7A:
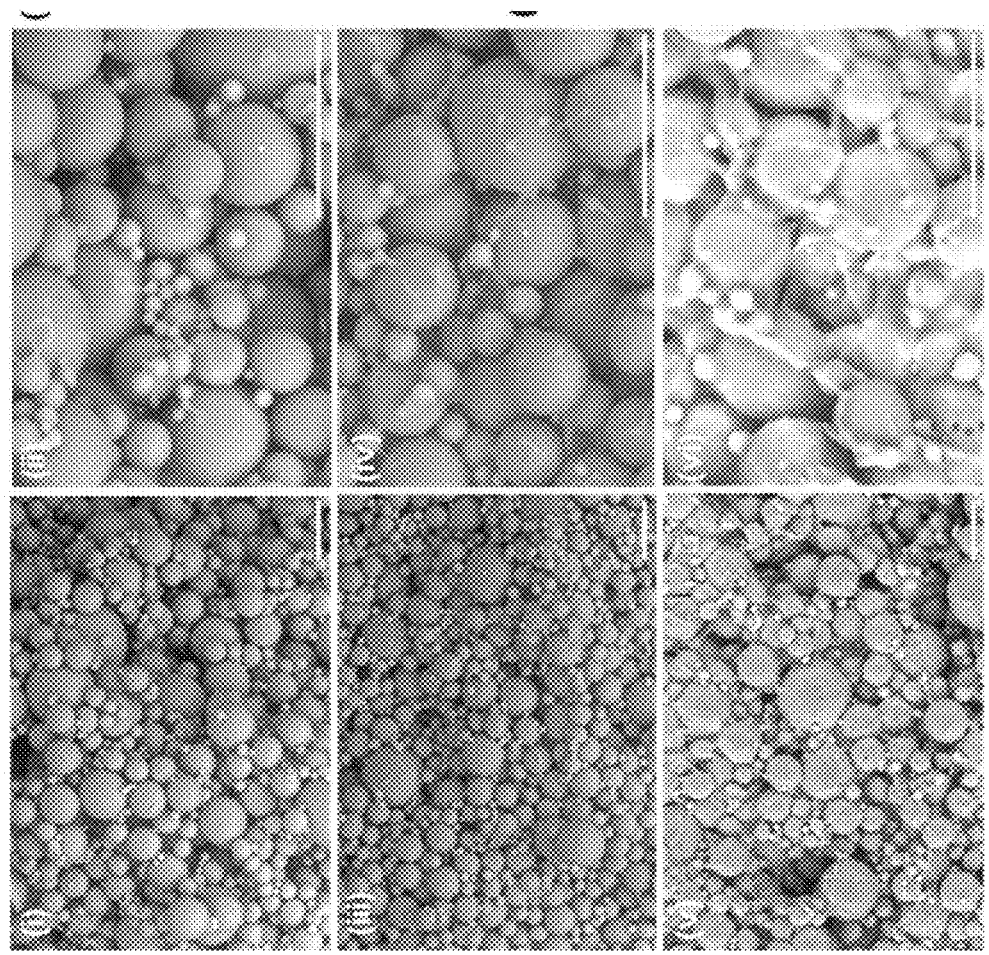
FIG. 7A shows SEM images of different microsphere hydrogel sponges: (i, ii) ST125, (iii, iv) ST250, and (v, vi) ST500 (the scale bar represents 50 μm)
Figure 7B:
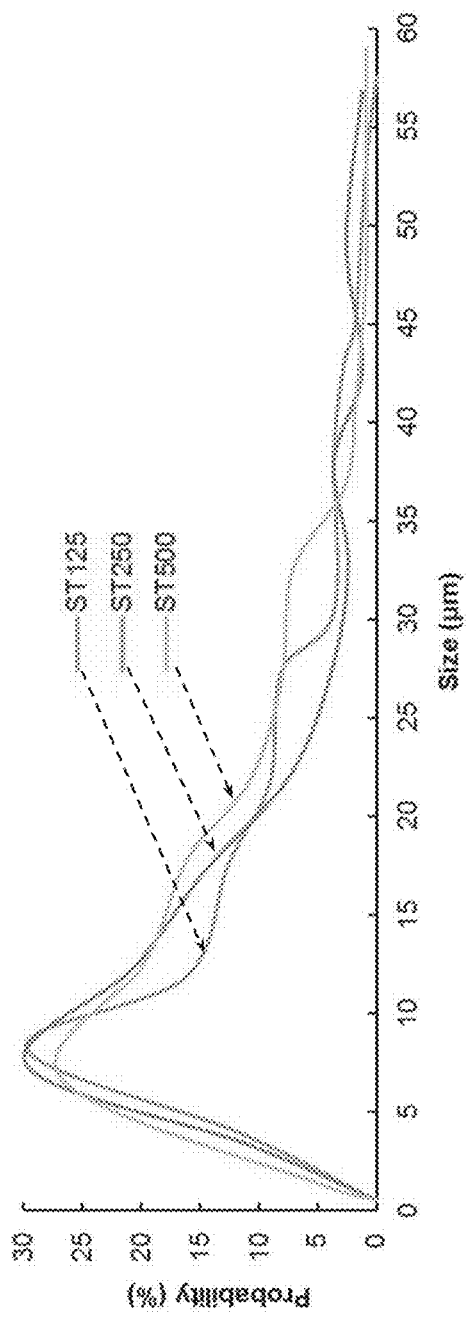
FIG. 7B is a graph showing the size distribution of the microspheres in different sponges ST125, ST250, ST500.
Figure 7D:
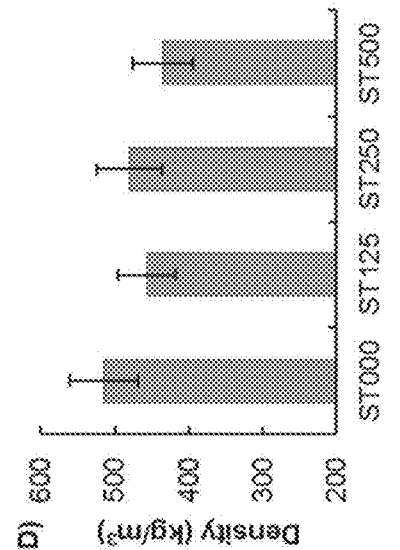
FIG. 7D is a graph showing the density of the sponges with different "starMA" concentrations.
Figure 7C:
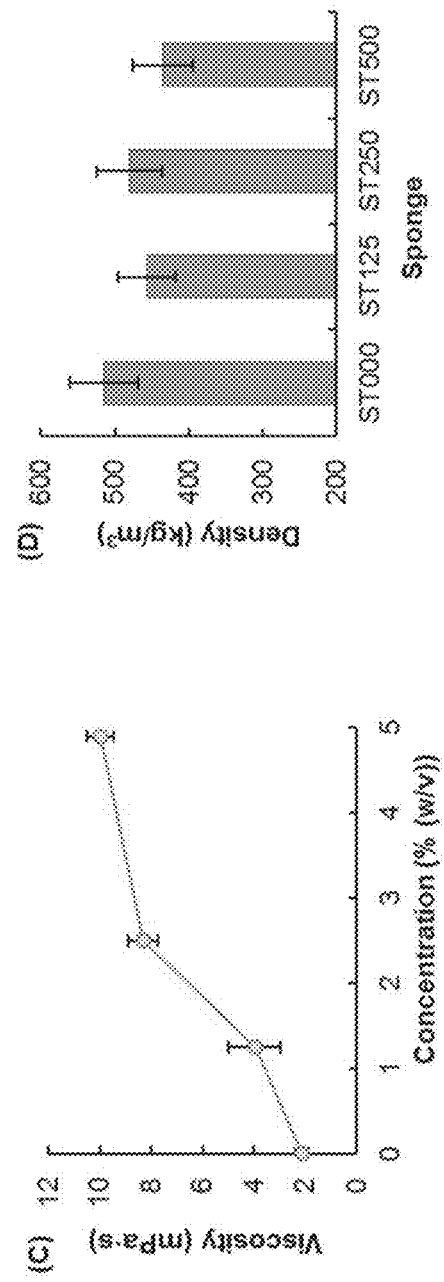
FIG. 7C is a graph showing the changes in the viscosity of the emulsion at different concentrations of "starMA" before UV curing.
Figure 9A:
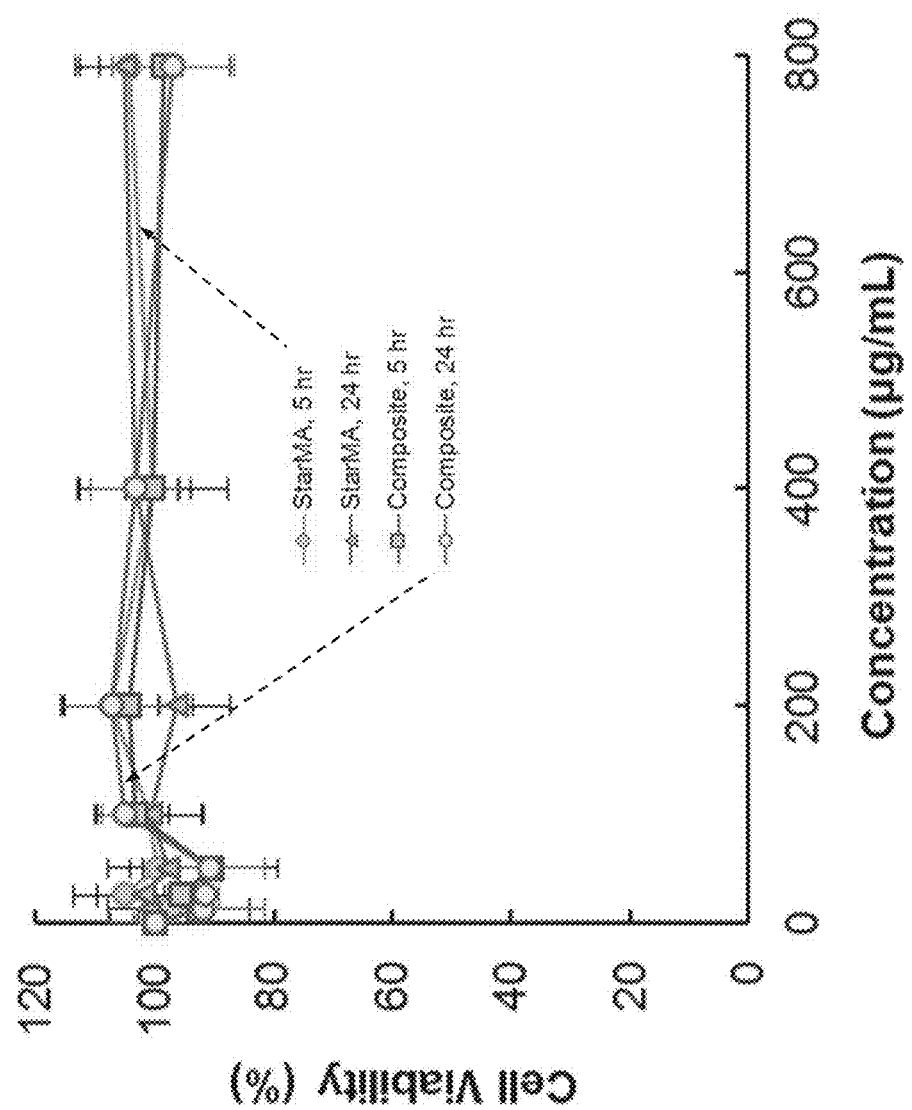
FIG. 9A is a graph showing the viability of HEK293 cells after different periods of treatment with "starMA" and the microsphere hydrogel sponge, without post-treatment incubation prior to the MTS assay (the overall concentration of "starMA" in the microsphere hydrogel sponges is 2.5 w/v %)
Figure 9B:
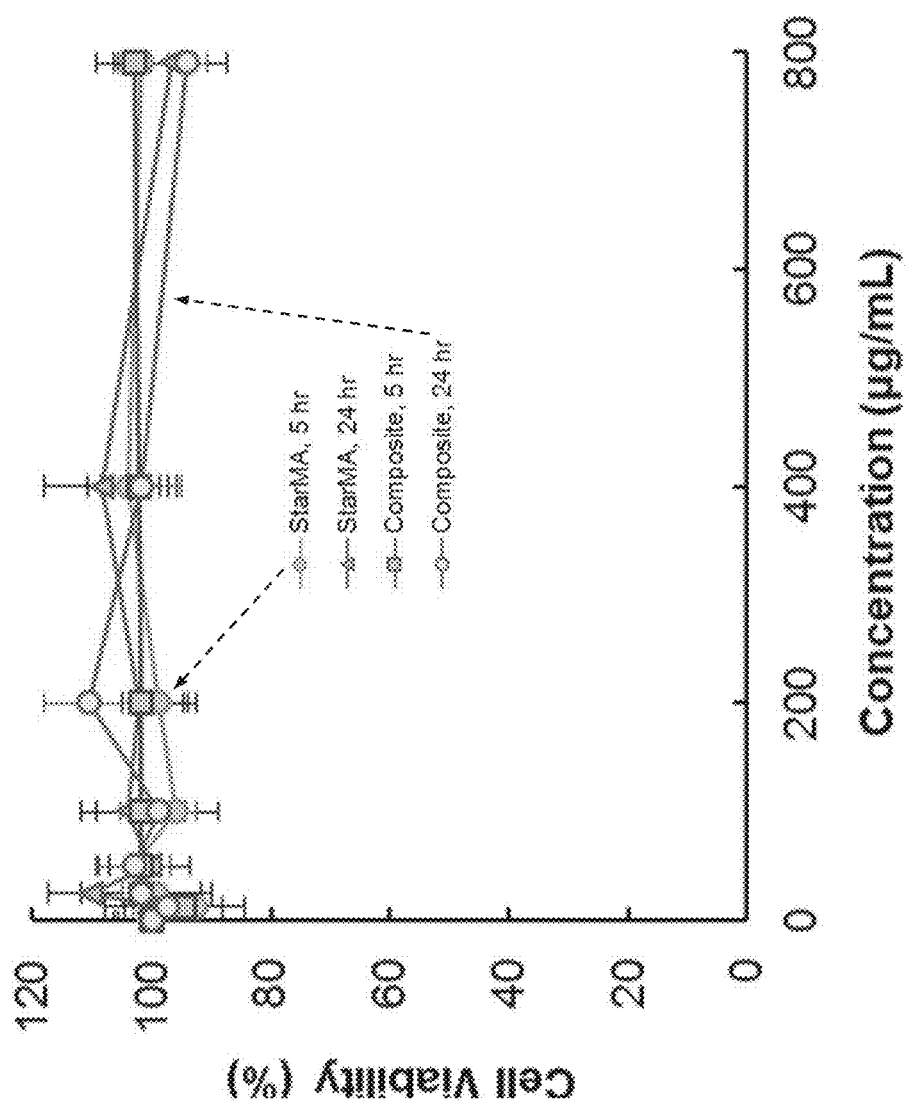
FIG. 9B is a graph showing the viability of HEK293 cells after different periods of treatment with "starMA" and the microsphere hydrogel sponge, with a 24-hour post-treatment incubation prior to the MTS assay (the overall concentration of "starMA" in the microsphere hydrogel sponges is 2.5 w/v %)
Figure 9C:
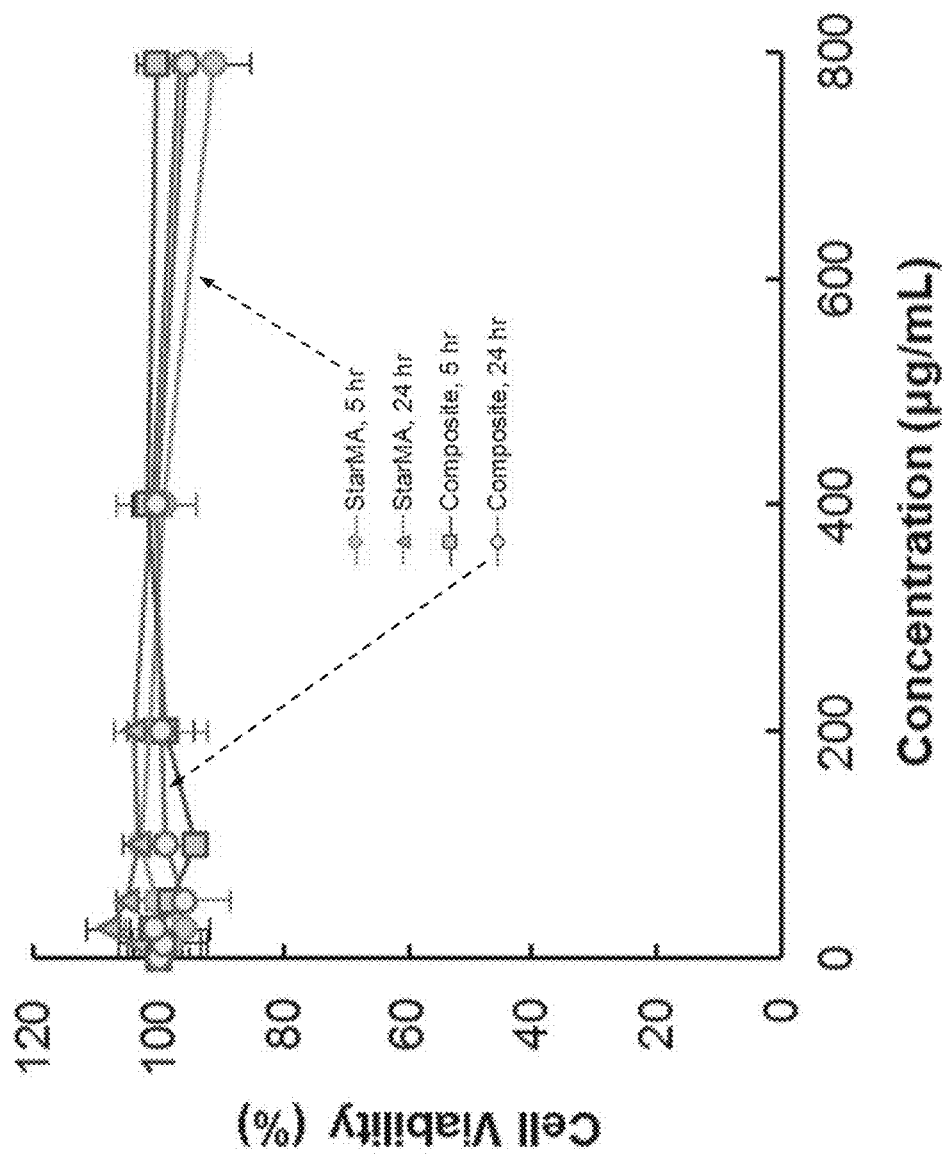
FIG. 9C is a graph showing the viability of 3T3 mouse fibroblasts after different periods of treatment with "starMA" and the microsphere hydrogel sponge, without post-treatment incubation prior to the MTS assay (the overall concentration of "starMA" in the microsphere hydrogel sponges is 2.5 w/v %)
Figure 9D:
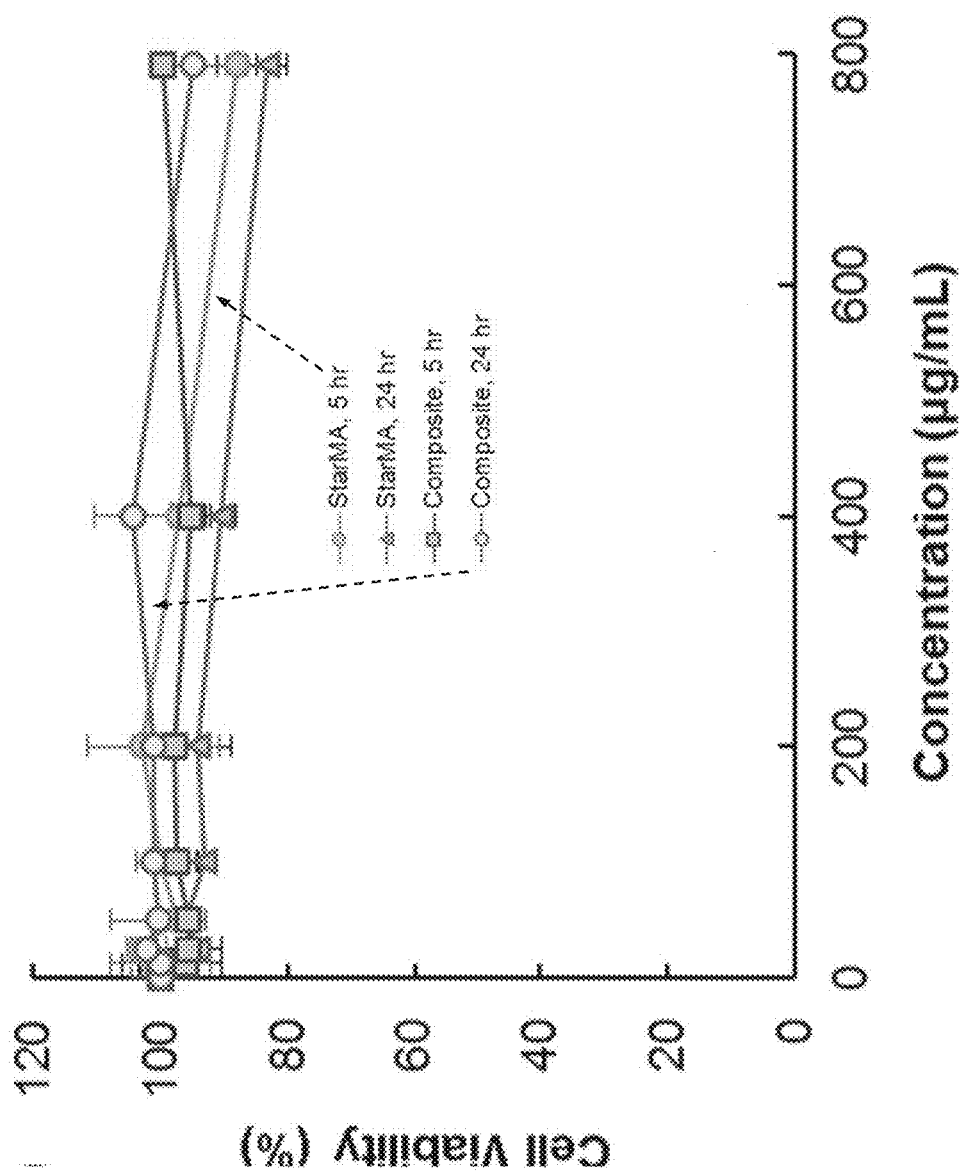
FIG. 9D is a graph showing the viability of 3T3 mouse fibroblasts after different periods of treatment with "starMA" and the microsphere hydrogel sponge, with a 24-hour post-treatment incubation prior to the MTS assay (the overall concentration of "starMA" in the microsphere hydrogel sponges is 2.5 w/v %)

By fixing the $V_{aq}/V_{oil}$ ratio to 1:1, the effect of the starMA concentration on the properties of the sponge in drug delivery is examined. The SEM images of the microstructures of sponges fabricated using different concentrations of starMA are shown in FIG. 7A. It can be observed that more starMA hydrogels are present inside the sponge when the starMA concentration increases. When the overall concentration of starMA increases from 1.25 w/v % to 5 w/v %, there is a significant decrease in the size of TMPETA microspheres and an increase in the viscosity of the emulsion system, but changes in the overall density of the sponge is not significant, as shown in FIG. 7B to 7D).

Due to the increase in the amount of starMA hydrogel present inside the sponge as the overall starMA concentration increases, it is expected that TMPETA microspheres inside the sponge can be hold more firmly together, thereby resisting expansion and erosion of the sponge. This is consistent with the observation in FIGS. 8A to 8C, in which an increase in the overall starMA concentration leads to a decrease in the swelling capacity, WAR, and erosion rate of the microsphere hydrogel sponge. An exception to this is ST000, in which the overall concentration of starMA is 0 w/v %. Due to its highly compact structure, diffusion of water molecules into ST000 is highly difficult. This may explain its extraordinarily high resistance to swelling and erosion.

Evaluation of Cytotoxicity

Low toxicity of a drug carrier is vital to its biomedical applications. The toxicity of starMA and the microsphere hydrogel sponge is studied using HEK293 cells3 and T3 mouse fibroblasts. HEK293 cells are selected because it is one of the commonly used cell lines in drug toxicology studies, particularly in assessing the effect of a drug candidate on the renal system. For 3T3 mouse fibroblasts, they are non-specific cell lines, with their viable rates being substrate-dependent. These cell lines, therefore, have a track record of use in cytotoxicity tests, and are adopted in this study for the MTS assay.

Based on the results shown in FIGS. 9A to 9D, no apparent loss of cell viability is observed immediately after treatment with different concentrations of the sponge and starMA. This indicates that acute cytotoxicity caused by the sponge is negligible. To determine the delayed cytotoxic effect of the sponge, treated cells are incubated for 24 hours before the MTS assay is performed. Loss of cell viability is negligible after 24 hours of post-treatment incubation. This indicates that the sponge has a high safety profile for possible development as a well-tolerated carrier for drug delivery.

Drug Loading and Release

As far as drug loading to polymeric materials is concerned, one of the existing approaches is to mix the drug directly with the polymer constituents during the fabrication of the systems, which will subsequently undergo chemical or physical cross-linking during which drugs will be entrapped. The efficiency of drug loading by this method, however, may be hindered if the drug to be loaded can undergo chemical reactions with constituents of the polymeric systems. Due to the low specificity of the cross-linking process during drug loading, side reactions may occur with the encapsulated bioactive agents and hence impede the drug activity and stability. In this regard, the sponge developed in the present embodiment is designed to allow for drug loading by adsorption to the extensive surface area provided by the microstructure of the sponge. This can prevent potential interactions between the drug and our sponge, thereby minimizing the loss of the drug activity during the drug loading process and rendering our system suitable to be used for delivery of fragile drugs such as nucleic acids and proteins.

Figure 10A:
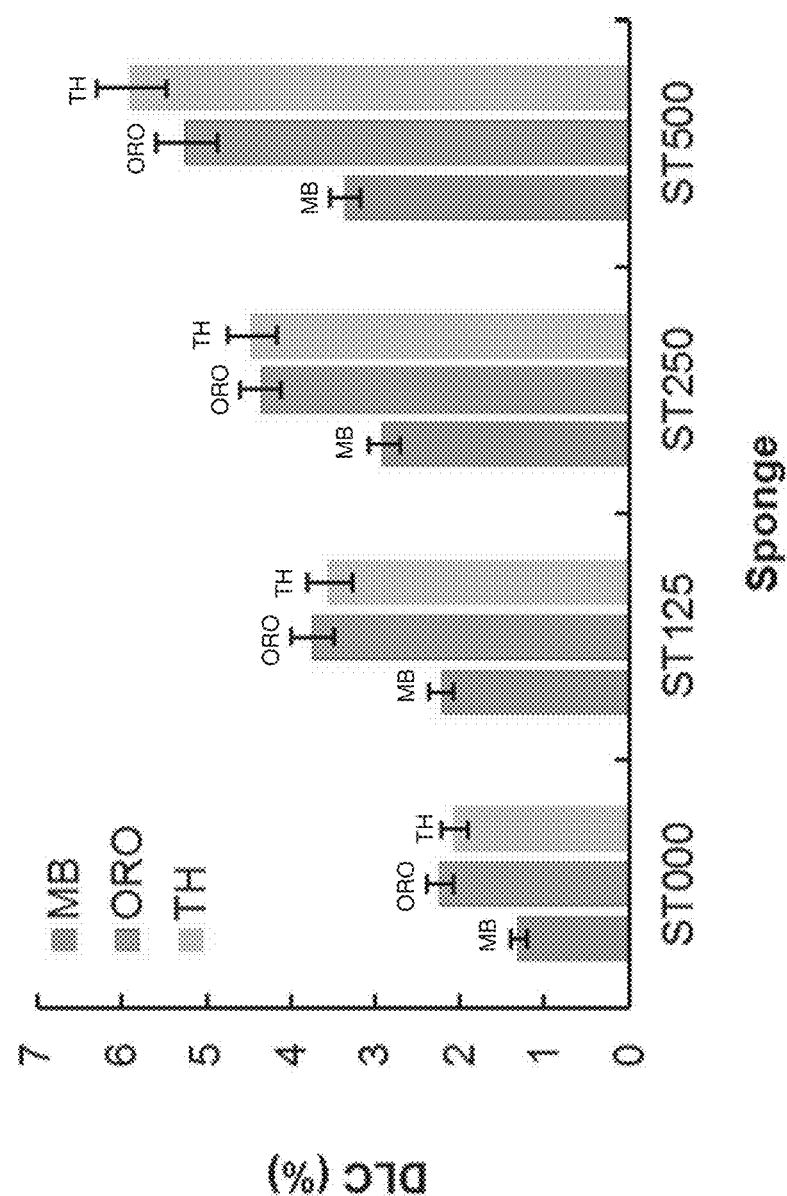
FIG. 10A is a graph showing the drug loading content of sponges with different "starMA" concentrations'.

To examine of performance of the sponges of the present embodiment in drug loading and release, MB, ORO and TH are selected as model drugs due to their varied aqueous solubility. The molecular weights of MB, ORO and TH are 319.9 g/mol, 408.5 g/mol, and 480.9 g/mol, respectively. Compared to ORO and TH, the DLC value (%) for MB is lower, as shown in FIG. 10A. This may be due to the smaller molecular weight of MB, which may diffuse out of the swollen sponge even before the completion of the loading process, thereby reducing the final drug loading yield achieved. However, it is also observed that an increase in the overall concentration of starMA has led to an increase in DLC. This can be explained by the observation that the water content, swelling capacity and erosion rate of the sponge decreases as the overall starMA concentration increases, as shown in FIGS. 8A-8C. Such changes in the sponge may reduce the loss of the adsorbed drug molecules during the drug loading process.

Figure 10B:
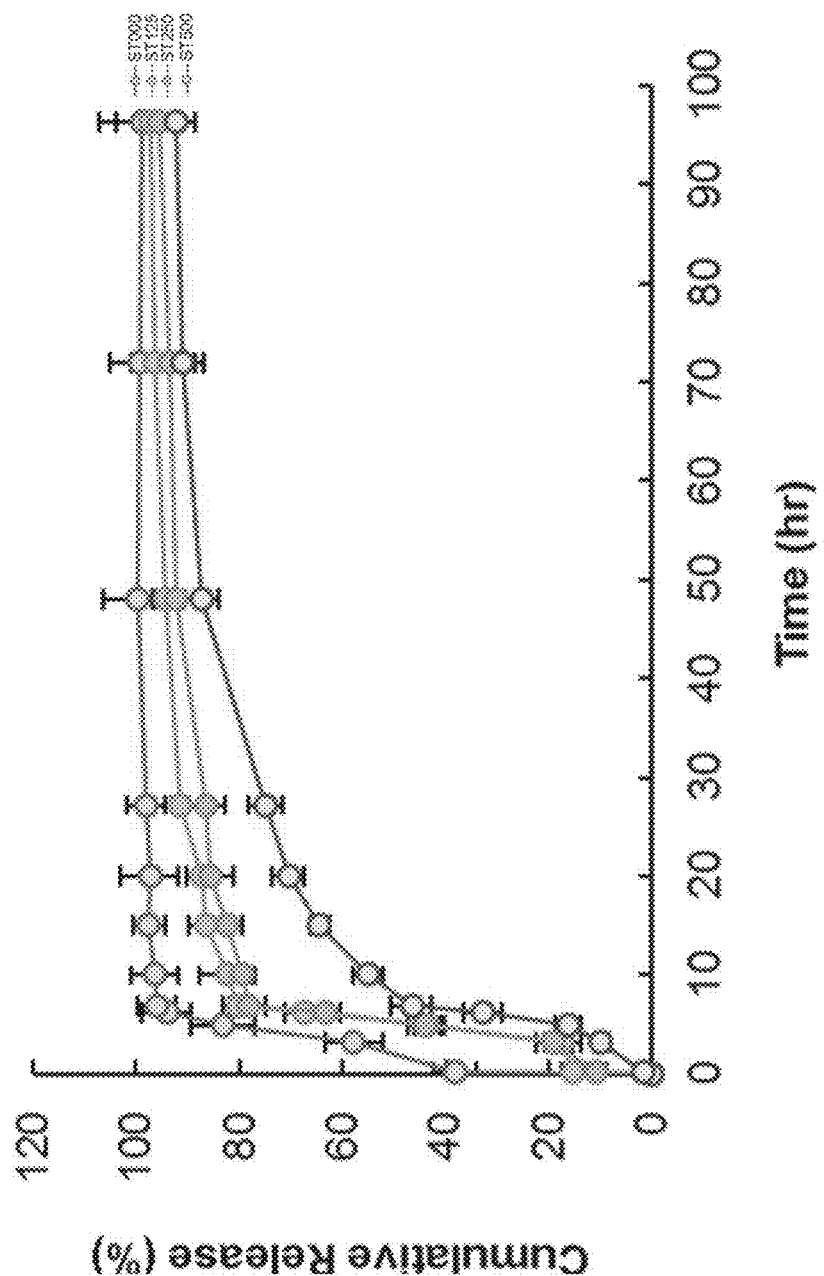
FIG. 10B is a graph showing the release profiles of MB-loaded sponges at 37° C. in deionized water.
Figure 10C:
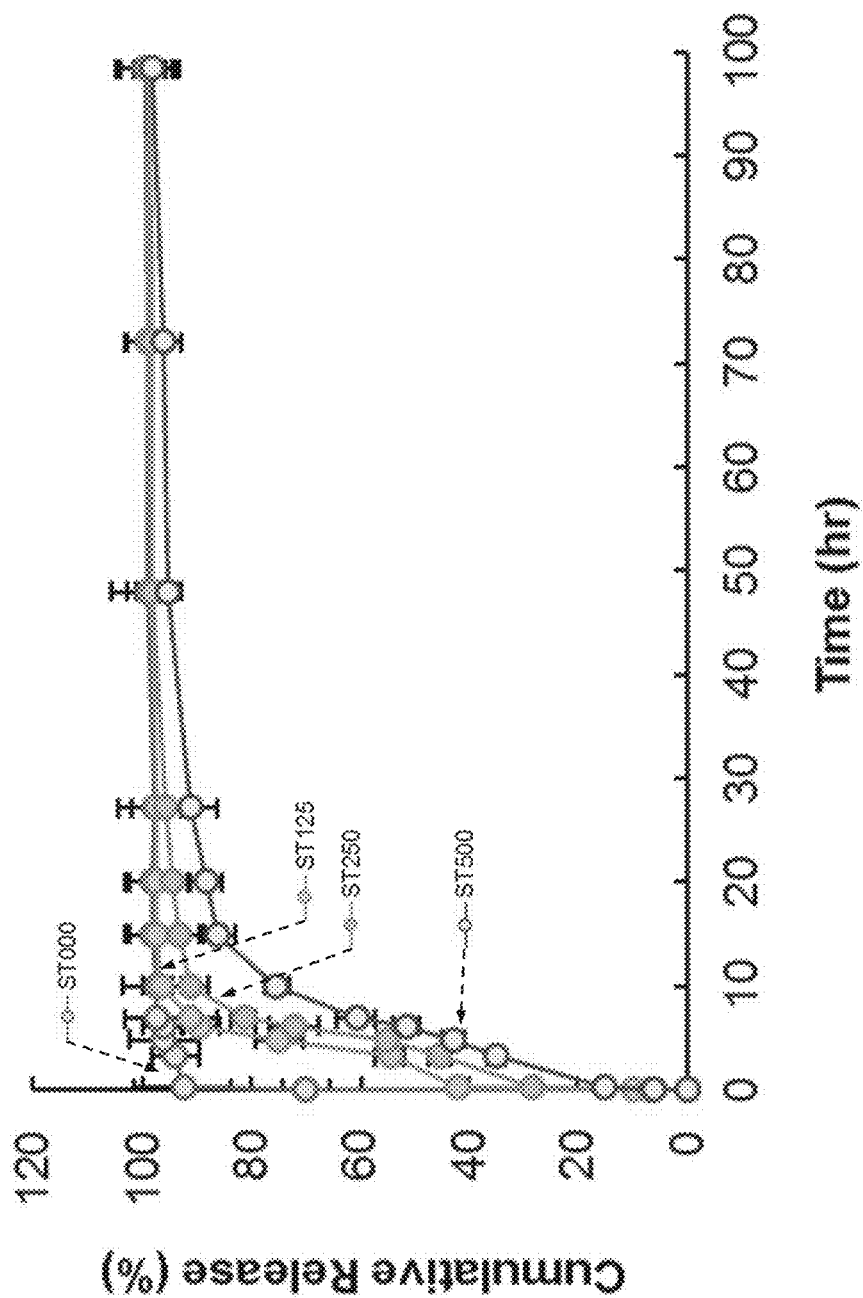
FIG. 10C is a graph showing the release profiles of ORO-loaded sponges at 37° C. in deionized water.
Figure 10D:
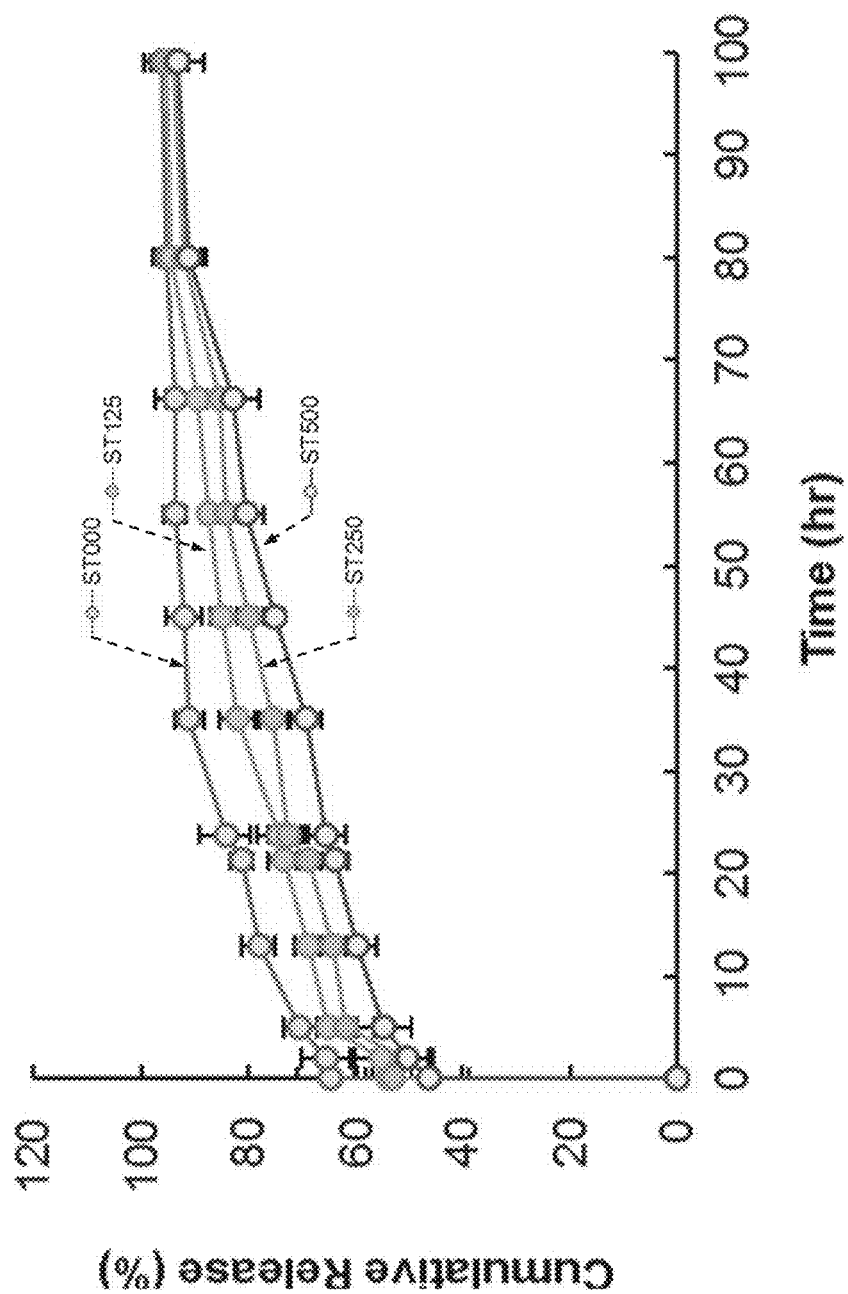
FIG. 10D is a graph showing the release profiles of TH-loaded sponges at 37° C. in deionized water.

To maintain constant therapeutic levels for prolonged periods and to reduce the total dose of administration, the ability of a carrier to prolong drug release is required. Compared to the control (ST000) in which the overall concentration of starMA is 0 w/v %, the drug release sustainability that the sponges in the present embodiment can sustain is substantially higher, as illustrated in FIGS. 10B-10D. The higher drug release sustainability of the sponge with a higher starMA concentration is attributed to the lower swelling capacity and erosion behaviour of the sponge, leading to more limited release of the drug. In addition, regardless of the overall concentrations of starMA in the sponges, the release of TH from the sponges is more sustainable as compared to that of ORO. The release of MB from the sponges is the least sustainable among the three model drugs adopted. This is attributed to the fact that an increase in the molecular weight of the model drug may reduce the diffusion rate of those drug molecules out of the swollen sponge, leading to a more sustained drug release profile.

Advantages

The above embodiments of the present invention have provided a hydrogel body (as also called "microsphere hydrogel sponge") that can be as a novel drug delivery device. In a preferred embodiment, the drug delivery device consists of poly(trimethylolpropane ethoxylate triacrylate) microspheres cross-linked by a hydrogel, which is formed by a starch-based bifunctional emulsion stabilizer (namely, starMA). The drug delivery devices of the present embodiments possess amphiphilic character and have a large surface area that is available for drug adsorption, and so can load both hydrophilic and lipophilic drugs, or more generally, drugs with various aqueous solubility, alone or simultaneously. The devices in the embodiments with a higher compositional ratio of the hydrogel have a low swelling capacity and erosion susceptibility, which lead to high drug release sustainability. The acute and delayed cytotoxic effects of the material in the present embodiments are found to be negligible, meaning that the drug carrier is safe for in vivo use. The drug delivery devices of the above embodiments are particularly adapted for applications at low dose levels and can provide sustained and controlled drug release. Also, the above embodiments of the drug delivery devices or material is easy to manufacture, and can be readily used for practical applications.

It should be noted that the drug release profiles of the device in the present invention can be tailored for specific applications, for example, by adjusting the ratio of the oil phase and aqueous phase. The above description does not list all possible alternatives, as the number of possible drug products (which require totally different drug release rates) in which the present invention can be used is too large.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A method of producing a drug delivery device, comprising:

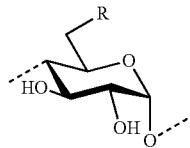

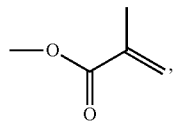

mixing target molecules in the form of where R is trimethylolpropane ethoxylate triacrylate, and initiator molecules to form an emulsion; and curing the emulsion using ultraviolet light or corresponding energy source, with the aid of the initiator molecules, to form, in a one-pot process, a microsphere hydrogel sponge with a porous body, the porous body being adapted for adsorption of drug molecules, wherein the porous body comprises:
a plurality of poly(trimethylolpropane ethoxylate triacrylate) microspheres, and
a hydrogel comprising the target molecules being cross-linked together in the form of

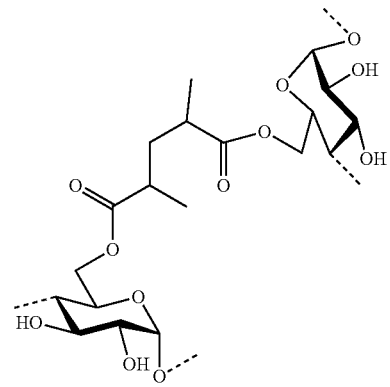

and forming cross-links connecting the plurality of poly (trimethylolpropane ethoxylate triacrylate) microspheres.

2. The method of claim 1, further comprising:
adsorbing lipophilic drug particles on the porous body.

3. The method of claim 1, further comprising:
adsorbing lipophilic drug particles and hydrophilic drug particles on the porous body.

4. The method of claim 1, further comprising forming the target molecules.

5. The method of claim 1 further comprising adsorbing hydrophilic drug particles on the porous body.

6. The method of claim 4, wherein forming the target molecules comprises:
(i) mixing a starch, a methacrylate source, and a catalyst; and
(ii) forming the target molecules using the mixed starch, methacrylate source, and catalyst.

7. The method of claim 6, wherein the catalyst comprises 4-Dimethylaminopyridine.

8. The method of claim 6, wherein step (ii) is performed at 50° C.

9. The method of claim 6, wherein the methacrylate source comprises glycidyl methacrylate.

* * * * *

UNITED STATES PATENT AND TRADEMARK OFFICE
CERTIFICATE OF CORRECTION

PATENT NO. : 11,123,434 B2
APPLICATION NO. : 15/656228
DATED : September 21, 2021
INVENTOR(S) : Wing Fu Lai and Andrei Rogatch It is certified that error appears in the above-identified patent and that said Letters Patent is hereby corrected as shown below:

In the Claims

Claim 1, Column 11, Lines 9-31 should read as follows: "1. A method of producing a drug delivery device, comprising: mixing target molecules in the form of

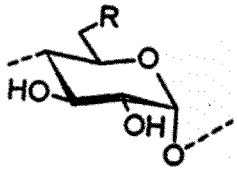

where R is

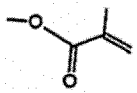

trimethylolpropane ethoxylate triacrylate, and initiator molecules to form an emulsion; and"

Signed and Sealed this
Eighth Day of March, 2022

Drew Hirshfeld
*Performing the Functions and Duties of the
Under Secretary of Commerce for Intellectual Property and
Director of the United States Patent and Trademark Office*